US008731679B2

(12) United States Patent
Ternes et al.

(10) Patent No.: US 8,731,679 B2
(45) Date of Patent: May 20, 2014

(54) IMPLANTABLE MEDICAL DEVICE CONFIGURATION BASED ON PORT USAGE

(75) Inventors: David J. Ternes, Roseville, MN (US); Shantha Arcot-Krishnamurthy, Vadnais Heights, MN (US); Jason J. Hamann, Blaine, MN (US); Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 142 days.

(21) Appl. No.: 13/084,754

(22) Filed: Apr. 12, 2011

(65) Prior Publication Data

US 2011/0270065 A1 Nov. 3, 2011

Related U.S. Application Data

(60) Provisional application No. 61/329,257, filed on Apr. 29, 2010.

(51) Int. Cl.
*A61N 1/365* (2006.01)

(52) U.S. Cl.
USPC .............. 607/59; 607/60; 607/115; 607/116; 600/372; 600/373; 600/377

(58) Field of Classification Search
USPC .............. 600/372–373, 377; 607/1–2, 59–60, 607/115–116
See application file for complete search history.

(56) References Cited

U.S. PATENT DOCUMENTS

| 4,628,934 | A | 12/1986 | Pohndorf et al. |
| 5,593,430 | A | 1/1997 | Renger |
| 7,236,826 | B2 * | 6/2007 | Lindh et al. ............ 607/27 |
| 7,463,928 | B2 | 12/2008 | Lee et al. |
| 8,160,328 | B2 * | 4/2012 | Goetz et al. ............ 382/128 |
| 2003/0018369 | A1 | 1/2003 | Thompson et al. |
| 2004/0078067 | A1 | 4/2004 | Thompson et al. |
| 2008/0091243 | A1 | 4/2008 | Ternes |

FOREIGN PATENT DOCUMENTS

| WO | WO-2004098063 A1 | 5/2004 |
| WO | WO-2009097224 A1 | 8/2009 |

OTHER PUBLICATIONS

"Australian Application Serial No. 2011245652, First Examination Report mailed Jan. 21 2013", 3 pgs.
"Australian Application No. 2011245642, Response filed May 16, 2013 to First Examination Report mailed Jan. 21, 2013", 26 pgs.
"International Application Serial No. PCT/US2011/032038, International Search Report mailed Jun. 14, 2011", 3 pgs.
"International Application Serial No. PCT/US2011/032038, International Preliminary Report on Patentability mailed Nov. 8, 2012", 7 pgs.
"International Application Serial No. PCT/US2011/032038, Written Opinion mailed Jun. 14, 2011", 6 pgs.
Japanese Application Serial No. N/A, Voluntary Amendment filed Oct. 31, 2012, With English Claims, 8 pgs.

* cited by examiner

*Primary Examiner* — Deborah Malamud
(74) *Attorney, Agent, or Firm* — Schwegman, Lundberg & Woessner, P.A.

(57) ABSTRACT

In an example, configuring an implantable medical device by determining port usage can include, receiving a port data object, determining a lead configuration, configuring access to a programmable parameter, and displaying a visual indication of the lead configuration. The port data object can be received from the implantable medical device and can include data associated with a port of the implantable medical device capable of connecting to a lead. The determining a lead configuration can be based on the port data object. The configuring access to a programmable parameter can be based on the lead configuration of the implantable medical device.

20 Claims, 11 Drawing Sheets

IMPLANTABLE MEDICAL DEVICE CONFIGURATION BASED ON PORT USAGE

CLAIM OF PRIORITY

This application claims the benefit of priority under 35 U.S.C. §119(e) of Ternes et al., U.S. Provisional Patent Application Ser. No. 61/329,257, entitled "IMPLANTABLE MEDICAL DEVICE CONFIGURATION BASED ON PORT USAGE", filed on Apr. 29, 2010, which is herein incorporated by reference in its entirety.

BACKGROUND

Certain patients exhibit a need for cardiac or neural stimulation. This stimulation can be achieved by using an implantable medical device. When such a need exists, cardiac tissue can receive cardiac electrostimulation. Such stimulation can evoke a resulting heart contraction, and can be used to maintain a rate of heart contractions that will meet a patient's metabolic need for cardiac output, or to spatially coordinate heart contractions so as to improve the heart's pumping efficiency. Similarly, non-cardiac neural tissue can receive neural stimulation, e.g., neurostimulation energy. Neurostimulation may be used to affect the autonomic balance between the sympathetic nervous system (which tends to speed up certain metabolic processes) and the parasympathetic nervous system (which tends to slow down certain metabolic processes). Some patients may benefit from both cardiac and neural stimulation.

In order to effectively meet the needs of patients requiring cardiac and/or neural stimulation, implantable medical device manufacturers have developed a variety of implantable medical devices. Cardiac rhythm management devices are one type of implantable medical device that monitor the heart, provide therapy to the heart, or both, and can incorporate cardiac or neural stimulation, or both. Typically the cardiac stimulation is provided through one or more leads configured specifically for cardiac stimulation. Neural stimulation is also typically delivered through one or more leads configured specifically for neural stimulation. In addition to leads configured for cardiac or neural stimulation, an implantable medical device can also include various sensors for sensing a variety of physiological parameters that can assist in delivering proper therapy to the patient.

Many modern implantable medical devices are capable of communicating with local or remote devices located outside of the body. These external devices can be used to receive information from the implantable medical device including sensor information and information about events, such as when the implantable medical device has provided therapy (also referred to as the device response). In some cases, the external communication or interface device can also transmit operational parameters to the implantable medical device, or in other words program the implantable medical device. An example external communication device is the LATITUDE® patient management system. Implantable medical devices, such as cardiac rhythm management devices, can be programmed with a number of different parameter settings that affect the manner in which therapy is delivered. Combined therapy devices include programmable parameters for each type of therapy that can be delivered by the device.

OVERVIEW

The present inventors have recognized, among other things, that potential challenges can arise in situations where an implantable medical device capable of both cardiac and neural stimulation is implanted with leads and sensors designed for only one type of therapy and/or sensing. One potential challenge arises if the programmable features of the implantable medical device related to the other type of stimulation remain active. Even in situations where the patient requires both cardiac and neural stimulation, it is common for different implantation procedures to be done for the different types of leads. Thus, the identified challenge can be present for some length of time between implantation procedures. Additionally, it is also not uncommon for physicians to implant a device capable of both cardiac and neural stimulation, but only enable one type of stimulation, which is capable of addressing the patient's current condition. The present inventors have also recognized, among other things, that physicians can waste valuable time with patients determining the lead and sensor configuration of the patient's medical device. In order to properly program or adjust a patient's medical device the physician needs to understand the lead and sensor configuration. The present system and methods can address these needs, such as by enabling the implantable medical device or external programming device to automatically determine the lead and sensor configuration such as by port usage, among other things.

Example 1 can include a method for configuring a programmable parameter of an implantable or other ambulatory medical device such as according to port usage. The method can include receiving a port data object, determining a lead configuration, and configuring access to a programmable parameter of the implantable medical device. The port data object can be received from an implantable medical device and can include data associated with a port of the implantable medical device capable of connecting a lead. The lead configuration associated with the implantable medical device can be determined based on the port data object. Access to a programmable parameter of the implantable medical device can be configured based on the lead configuration.

In Example 2, the method of Example 1 can optionally include a measurable attribute for the port within the port data object.

In Example 3, the method of any one of Examples 1-2 can optionally include an impedance measurement as the measurable attribute within the port data object.

In Example 4, the method of any one of Examples 1-3 can optionally include determining whether the impedance measurement indicates one of the following conditions: an open circuit; a short circuit; or an impedance being within a specified range of impedance.

In Example 5, the method of any one of Examples 1-4 can optionally include a manual override indicator within the port data object, the manual override indicator indicates a lead configuration for a port of the implantable medical device.

In Example 6, the method of any one of Examples 1-5 can optionally include determining the lead configuration, including determining a therapy type, and wherein the configuring access includes enabling a programmable parameter based on the therapy type.

In Example 7, the method of any one of Examples 1-6 can optionally include displaying a visual indication of the lead configuration of the implantable medical device.

In Example 8, the method of any one of Examples 1-7 can optionally include displaying a graphical display representing the implantable medical device as a visual indicator.

In Example 9, the method of any one of Examples 1-8 can optionally include determining whether a port is configured for one type of use from a group of potential uses including: unused; sense-only; therapy only; or therapy with sensing. In an example, a device can include a port which can be configured for any two uses recited above, e.g., unused or sense-only. In another example, a device can include a port which can be configured for any three uses recited above, e.g., sense-only, therapy only, or unused. In yet another example, a device can include a port which can be configured for all four uses recited above.

In Example 10, the method of any one of Examples 1-9 can optionally include determining a therapy output restriction associated with a port.

Example 11 can include a system for configuring a programmable parameter of an implantable or other ambulatory medical device such as according to port usage. The system can include an external device, configured to communicate with an implantable medical device. The external device can be configured to receive from the implantable medical device a port data object, the port data object including data associated with a plurality of ports used by the implantable medical device to connect to a plurality of leads. The external device can also be configured to determine, based on the port data object, a lead configuration of the implantable medical device. The external device can further be configured to configure, based on the lead configuration associated with the implantable medical device, access to a programmable parameter of the implantable medical device.

In Example 12, the system of Example 11 can include the external device being optionally configured to receive the port data object including a measurable attribute associated with each of the plurality of ports represented within the port data object.

In Example 13, the system of any one of Examples 11-12 can include the external device optionally configured to receive an impedance measurement as the measurable attribute associated with individual ones of the plurality of ports.

In Example 14, the system of any one of Examples 11-13 can include the external device optionally configured to determine the lead configuration based on determining whether the impedance measurement associated with individual ones of the plurality of ports indicates one of the following conditions: an open circuit; a short circuit; or an impedance being within a specified range of impedance.

In Example 15, the system of any one of Examples 11-14 include the external device optionally configured to determine the lead configuration based on detecting whether the port data object includes a manual override indicator for any of the plurality of ports, wherein the manual override indicator indicates that the port is unused.

In Example 16, the system of any one of Examples 11-15 include the external device optionally configured to determine the lead configuration based on determining a therapy type, and wherein the external device configures access to a plurality of programmable parameters based on enabling the plurality of programmable parameters associated with the therapy type.

In Example 17, the system of any one of Examples 11-16 optionally includes a display device, communicatively coupled to the external device, where the display device can be configured to display a visual indication of the lead configuration of the implantable medical device.

In Examples 18, the system of any one of Examples 11-17 optionally includes a display device configured to display a graphical display representing the lead configuration of the implantable medical device.

In Example 19, the system of any one of Examples 11-18 include the external device optionally configured to determine a lead configuration based on determining, from the port data object, whether a port is configured for a type of use selected from a group of potential uses including: unused; sense-only; therapy only; and therapy with sensing.

In Example 20, the system of any one of Examples 11-19 include the external device optionally configured to determine a lead configuration based on determining, from the port data object, whether a lead connected to a port includes a therapy output restriction.

Example 21 can include a processor-readable storage medium comprising instructions, which when implemented by one or more processors perform operations to automatically configure programmable parameters of an implantable or other ambulatory medical device such as according to port usage. The instructions can include an operation to receive from an implantable medical device a port data object, the port data object can contain data associated with a port of the implantable medical device capable of connecting a lead. The instructions can also include an operation to determine, based on the port data object, a lead configuration associated with the implantable medical device. The instructions further can include an operation to configure, based on the lead configuration associated with the implantable medical device, access to a programmable parameter of the implantable medical device, and an operation to display a visual indication of the lead configuration of the implantable medical device.

In Example 22, the processor-readable storage medium of Example 21 can include instructions to optionally perform an operation to receive a measurable attribute for the port within the port data object.

In Example 23, the processor-readable storage medium of any one of Examples 22-23 includes instructions to optionally perform an operation to receive an impedance measurement as the measurable attribute within the port data object.

In Example 24, the processor-readable storage medium of any one of Examples 21-23 can include instructions to optionally perform an operation to determine whether the impedance measurement indicates one of the following conditions: an open circuit; a short circuit; or an impedance being within a specified range of impedance.

In Example 25, the processor-readable storage medium of any one of Examples 21-24 can include instructions to optionally perform an operation to receive, as part of the port data object, a manual override indicator, the manual override indictor indicating that the port is unused.

In Example 26, the processor-readable storage medium of any one of Examples 21-25 can include instructions to optionally perform an operation to determine a therapy type, and wherein the configuring access includes enabling programmable parameters based on the therapy type.

In Example 27, the processor-readable storage medium of any one of Examples 21-26 can include instructions to optionally perform an operation to display a graphical display representing the implantable medical device as the visual indicator.

In Example 28, the processor-readable storage medium of any one of Examples 21-27 can include instructions to optionally perform an operation to determine whether a port is configured for a type of use selected from a group of potential uses including: unused; sense-only; therapy only; and therapy with sensing.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
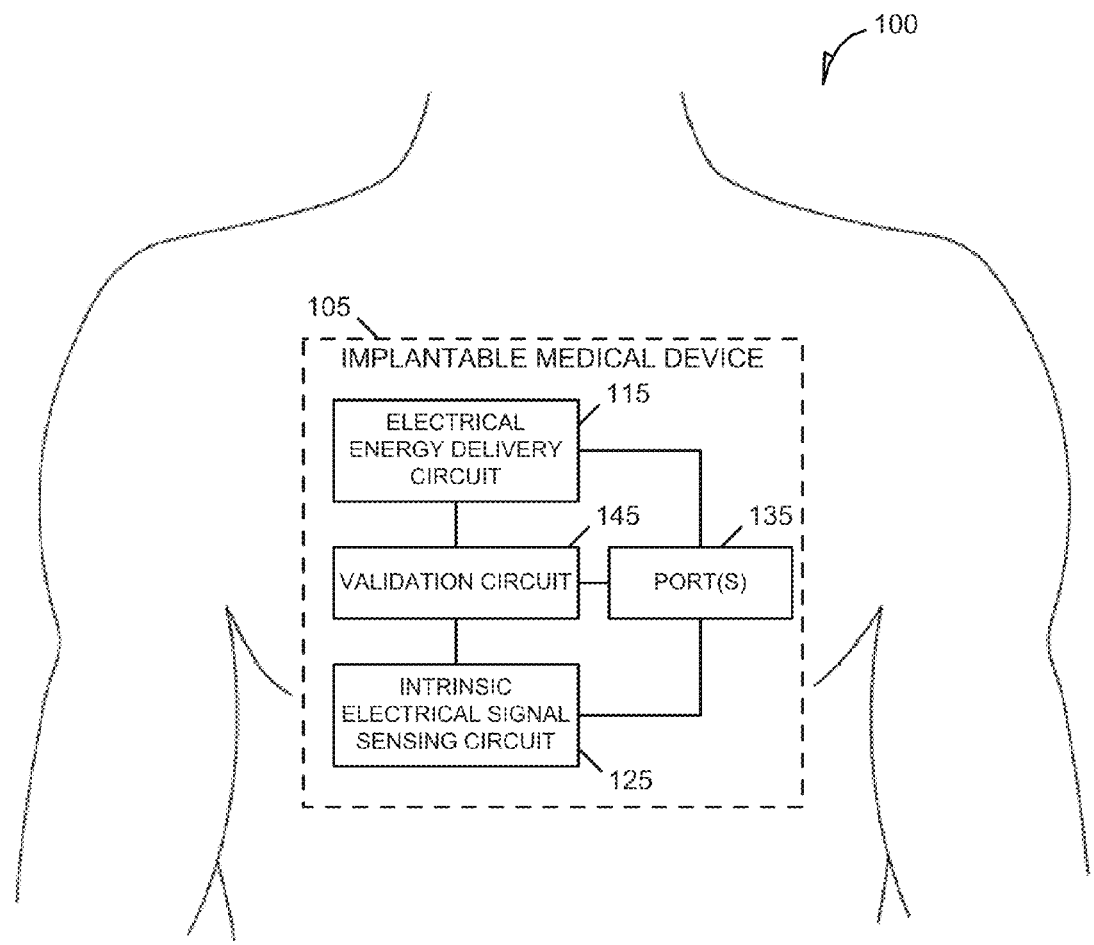
FIG. 1 illustrates generally an example of a system including an implantable medical device, which includes an electrical energy delivery circuit, an intrinsic electrical signal sensing circuit, one or more ports, and a validation circuit.

As described above, some implantable or other ambulatory medical devices can be used to provide physiological monitoring or pacing or other therapy to patients who have cardiac rhythm problems. For example, an implanted CRM device can be used to provide pacing therapy to a patient with sinus node dysfunction, where the heart fails to properly initiate depolarization waves, or an atrio-ventricular condition disturbance, wherein the conduction of depolarization waves through the heart tissue is impaired.

Implantable medical devices can also be used to deliver Autonomic Modulation Therapies (AMT) (also may be referred to as NeuroCardiac Therapy (NCT)) alone or in conjunction with pacing or other cardiac resynchronization therapy. AMT can be provided in a combined therapy device that provides one or more of the following therapies: AMT, AMT diagnostics, closed-loop AMT, bradycardia therapies, tachycardia therapies, and cardiac resynchronization therapies, among others.

Physicians implanting a device to treat certain symptoms can implant a combined therapy device while either temporarily or permanently only using some of the available therapies. Physicians will often choose a device they are most familiar with or that is considered the best device on the market. The most advanced devices can often include combined therapy devices. Physicians can also choose to implant a combined therapy device to enable the use of additional therapies in the future without the need to replace the implanted device.

In situations where a combined therapy device is implanted with the intention of using multiple therapies, there is often a period of time when only one of the available therapies is used. For example, if the device is going to be used for both cardiac and neural therapies, the leadwire or catheter (hereinafter referred to collectively as "leads") used to deliver each therapy often requires different implantation procedures. The separate procedures will often result in a timeframe where the device may be capable of providing a therapy that the device and associated leads are not configured to deliver.

Enabling the combined therapy device (or programming device) to prevent configuration of parameters or therapies that the device is not physically configured to provide can prevent potential operational challenges and save time for a treating physician. One technique for enabling a combined therapy device to prevent configurations not currently supported by the connected leads or sensors, is to interrogate the ports used to connect the leads and sensors to determine what type of leads or sensors are connected. In an example, the port usage information gathered through port interrogation can be used to configure the implanted device. For example, the implanted device can enable the programmable parameters associated with available therapies and disable programmable parameters associated with the unavailable therapies. In another example, the port usage information can be communicated to an external programming device. In this example, the external programming device can enable functions associated with the available therapies and disable functions associated with the unavailable therapies.

The remainder of the detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

Implantable Device and Related Systems

FIG. 1 is a block diagram illustrating generally an example of portions of a system 100 including an implantable medical device 105, which includes an electrical energy delivery circuit 115, a sensing circuit 125, a port 135, and a validation circuit 145.

In this example, one or more ports 135 are configured to couple the electrical energy delivery circuit 115 and the sensing circuit 125 to at least one tissue site in the body. In other examples, the ports 135 can include a single port, or more than one port, to couple one or both of the electrical energy delivery circuits 115 and the sensing circuit 125 to a single tissue site, or to more than one tissue site, in the body. Thus, a single port can connect to an electrode to contact a single tissue site, or to different electrodes respectively located at more than one tissue site, or more than one port can connect to a single tissue site or more than one tissue site.

In an example, the ports 135 connect the implantable medical device 105 to at least one tissue site in the body using at least one leadwire or catheter (referred to as a "lead"), where each lead includes one or more electrodes to contact the at least one tissue site. In other examples, the ports 135 can include any electrical connector between the implantable medical device 105 and an electrical connection to the tissue site. In an example, the ports 135 can also connect sensors used to sense physiological parameters that can be used by the implantable medical device 105 to assist in delivery therapy or in providing diagnostic information to a treating physician.

In the example of FIG. 1, the implantable medical device 105 can include a cardiac stimulator, such as a pacer or cardiac resynchronization therapy (CRT) device to deliver a pacing or resynchronization energy to contractile cardiac tissue, or a neural stimulator, such as a vagal nerve stimulator (VNS) device to deliver a neurostimulation energy to a non-contractile cardiac or non-cardiac neural tissue, or both. In an example, the implantable medical device 105 can provide a shocking energy, such as a defibrillation energy. The implantable medical device 105 can include any device configured to deliver an electrical energy to a cardiac tissue, any device configured to deliver an electrical energy to a neural tissue, or any device configured to delivery an electrical energy to a cardiac tissue as well as a neural tissue.

The sensing circuit 125 can be configured to receive an intrinsic electrical signal from a tissue site in the body, such as via a lead that can be coupled to the sensing circuit 125 of the implantable medical device 105. An intrinsic electrical signal can also include an electrical characteristic of a tissue site in the body, e.g., the electrical impedance at a tissue site. In an example, the sensing circuit 125 is configured to receive more than one intrinsic electrical signal from one or more tissue sites in the body. The sensing circuit 125 can also be configured to receive data from one or more other physiological sensors connected to the implantable medical device 105.

In the example of FIG. 1, the validation circuit 145 can be coupled to the electrical energy delivery circuit 115 and the sensing circuit 125. In an example, the validation circuit 145 can be included in the implantable medical device 105. In other examples, the validation circuit 145 can be an external component or part of an external programming device. The validation circuit 145 generally can determine an indication of the type of lead or sensor coupled to the one or more ports 135. In an example, the validation circuit 145 can receive an intrinsic electrical signal from the sensing circuit 125 and can use the intrinsic electrical signal to determine the indication of the lead type coupled to the one or more ports 135. In an example, the validation circuit 145, upon determining the indication of the lead type, can enable or inhibit one or more programmable parameters or one or more configurations of the implantable medical device 105. In an example, the validation circuit 145, upon determining the indication of lead type, can enable or inhibit access to one or more related programmable parameters or configurations of the implantable medical device 105.

Figure 2A:
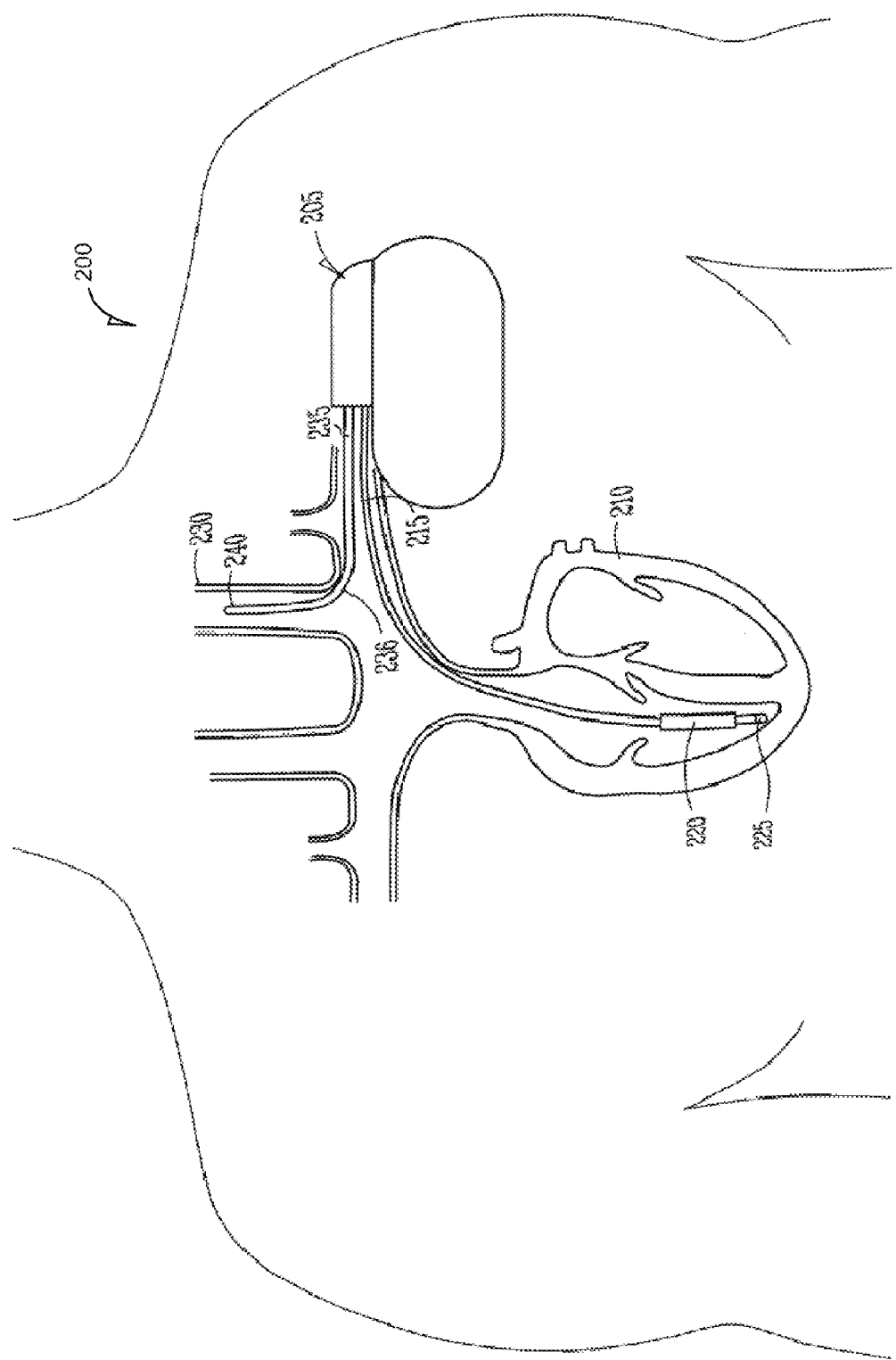
FIG. 2A illustrates generally an example of a system including an implantable device and more than one port for both cardiac and neural stimulation.
Figure 2B:
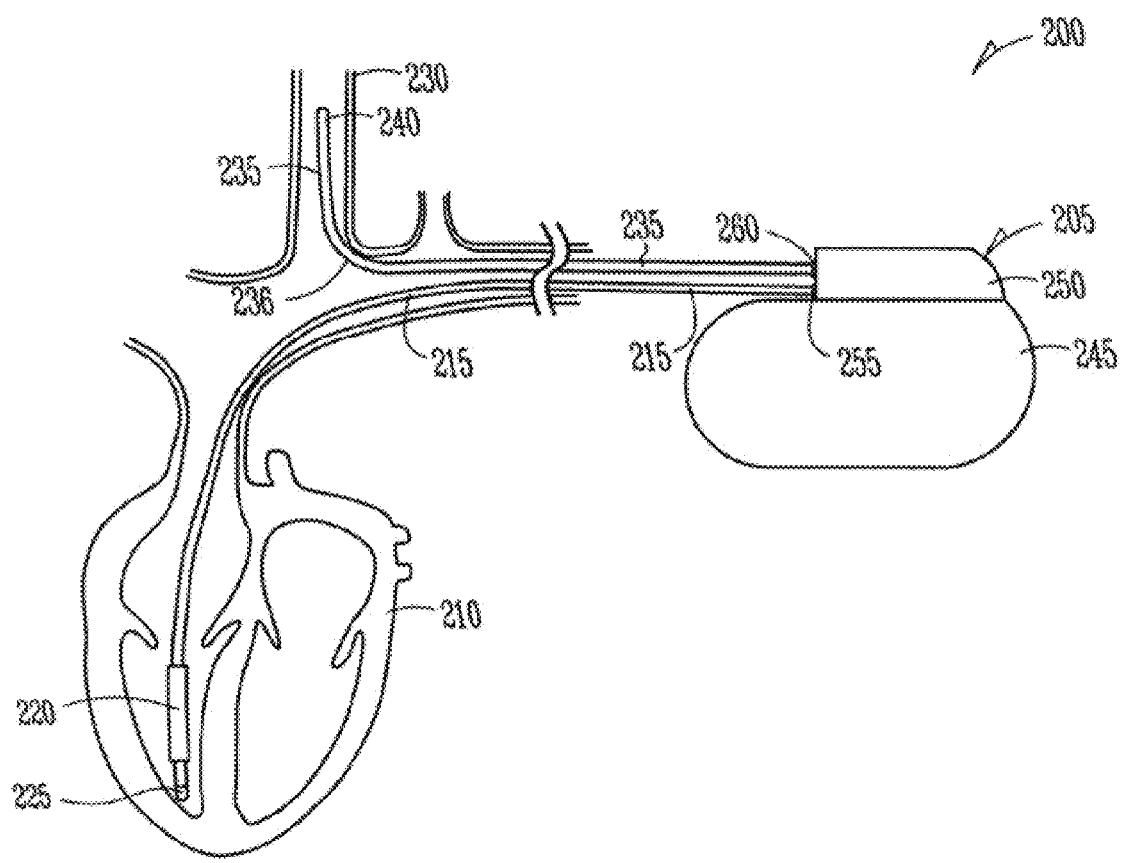
FIG. 2B illustrates generally an example of a system including an implantable device and more than one port for both cardiac and neural stimulation.

FIGS. 2A and 2B are block diagrams illustrating generally an example of a system 200 including an implantable medical device 205. In an example, the implantable medical device 205 can include a header 250 having more than one port, e.g., a first port 255 and a second port 260, such as to permit both cardiac and neural stimulation. In an example, a port, e.g., a first port 255 or a second part 260, can be configured to deliver more than one type of therapy via time-multiplexing (or some similar mechanism). Examples of the implantable medical device 205 can include any device capable of providing neural and/or cardiac stimulation.

In an example, the implantable medical device 205 can include a hermitically-sealed or similar housing 245 coupled to the header 250. The header 250 can include one or more than one port, e.g., the first port 255 or the second port 260.

In an example, such as shown in FIGS. 2A and 2B, the system 200 can include a first lead 215 coupled to the first port 255. In an example, the first lead 215 can be configured to provide stimulation to the heart 210 or sense an intrinsic cardiac signal of the heart 210. An intrinsic cardiac signal can include any signal indicative of cardiac activity, e.g., an internal electrocardiogram signal (ECG). In an example, the first lead 215 can include a single electrode, e.g., a tip electrode 225, or more than one electrode, e.g., the tip electrode 225 and a ring electrode 220. In other examples, the housing 245 can include an electrode, such as a "case" or a "can" electrode, or the header 250 can include an electrode, such as an indifferent electrode.

In an example, system 200 can further include a second lead 235 coupled to the second port 260. In an example, the second lead 235 can be configured to provide stimulation to a nerve, e.g., the vagal nerve, or to sense an intrinsic neural signal. An intrinsic neural signal can be any signal indicative of neural activity. In other examples, the second lead 235 can include a portion configured to be located in the jugular vein 230 and can include a distal end 240, which can include a nerve stimulation electrode located at or near the distal end 240. In an example, the second lead 235 can include a bend 236 associated with the location of the second lead 235, such as in the jugular vein 230. In yet other examples, the second lead 235 can include a cuff electrode, which can be configured to provide stimulation to a nerve or to sense an intrinsic neural signal.

In an example, the nerve stimulation electrode located at or near the distal end 240 of the second lead 235 can have a certain surface area. In these examples, the sensing circuit 125 can be used to measure the amount of impedance associated with the lead to determine the approximate surface area. For example, nerve stimulation leads with 60 mm$^2$ can exhibit an impedance of approximately 60Ω. In another example, an impedance measurement in the range of 50Ω to 70Ω can indicate a lead surface area of 60 mm$^2$. In these examples, the impedence measurement is measuring an impedance internal to the lead. In an example, the impedance measurement can include a measurement between therapy electrodes with tissue between them. The tissue can affect the impedence measurement.

In an example, the system 200 includes a single port, e.g., the first port 255, configured to either provide stimulation to the heart 210 or to sense an intrinsic cardiac signal of the heart 210, or to provide stimulation to a nerve, e.g., the vagal nerve, or to sense an intrinsic neural signal.

Figure 3:
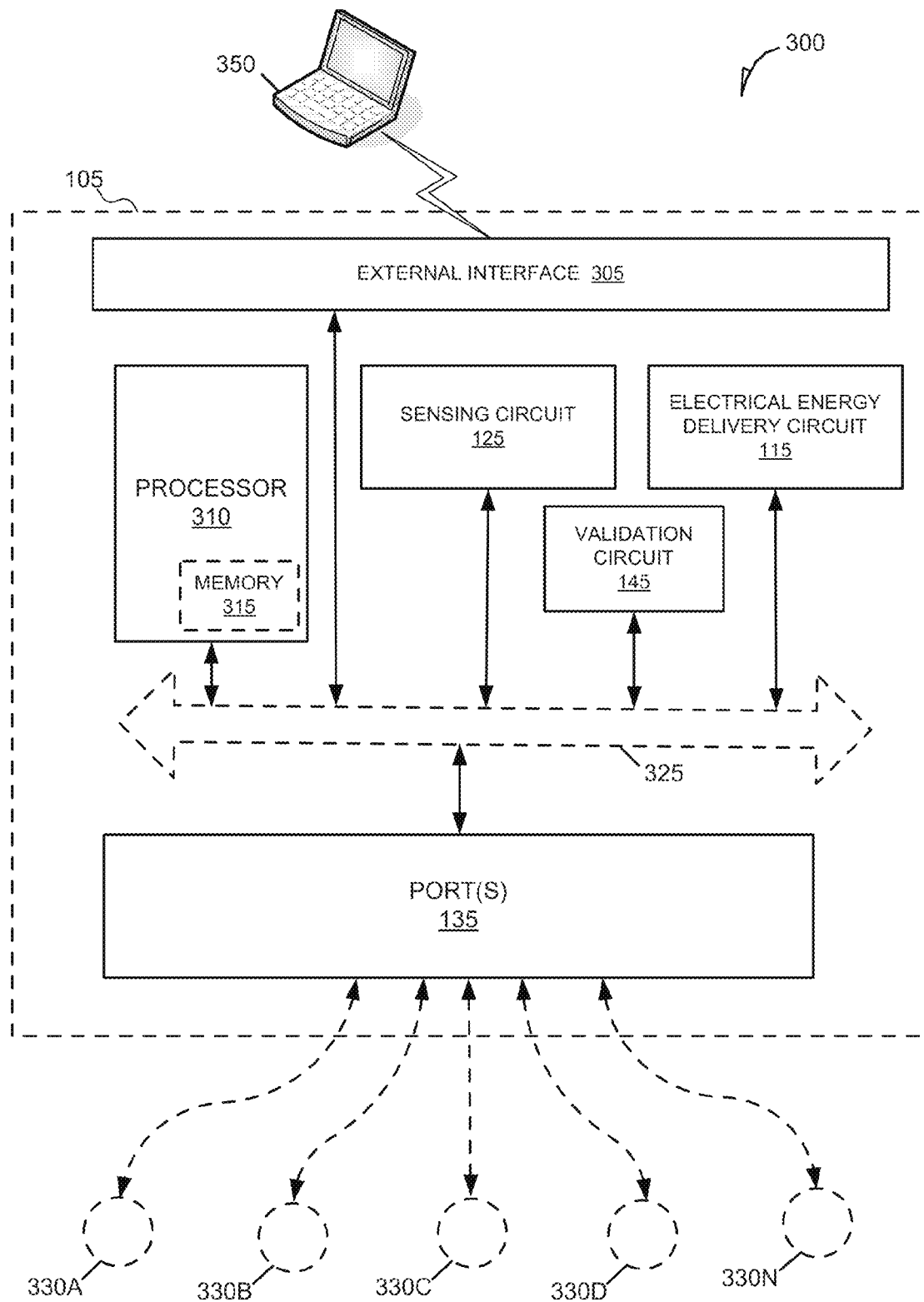
FIG. 3 illustrates generally an example of a system including an implantable device and an external device for configuring the implantable device based on port usage.

FIG. 3 illustrates generally an example of a system 300 including an implantable medical device 105 and an external device 350, where the external device 350 can be used for configuring the implantable medical device 105 based on port usage. In an example, the system 300 can include the implantable medical device 105, one or more leads and/or physiological data sensors 330A, 330B, . . . , 330N (collectively hereinafter referred to as lead(s) 330), and the external device 350. In an example of the system 300, the implantable medical device 105 can include the sensing circuit 125, the electrical energy delivery circuit 115, the validation circuit 145, one or more ports 135, an external interface 305, a processor 310, and optionally a communication bus 325. In an example, the processor 310 can include a memory 315. In an example, the communication bus 325 can be used to facilitate communication between the different circuits, e.g., sensing circuit 125, electrical energy delivery circuit 115, and the validation circuit 145, and the processor 310.

In an example, an external programming device, such as the external device 350, can communicate with the implantable medical device 105 over the external interface 305. The external interface 305 can represent a wired or wireless communication mechanism.

In an example, the implantable medical device 105 can receive physiological sensor data from one or more leads 330 through one or more ports 135. In an example, the leads 330 can include sensors implanted within the patient's body, also referred to as internal sensors. In other examples, the leads 330 can include ambulatory or other external sensors such as worn or carried by the patient or adhered to a patient's skin or worn against a patient's skin In an example, the leads 330 can include both external and internal sensors. A non-exhaustive list of examples of sensors represented by leads 330 can include a cardiac signal sensing circuit, an intracardiac impedance sensing circuit, a transthoracic impedance sensing circuit, a blood pressure sensor, a blood gas sensor, a chemical sensor, a heart sound sensor, a posture sensor, and an activity sensor. As discussed above in reference to FIGS. 2A and 2B, the leads 330 can also be used to deliver various neural and/or cardiac therapies, e.g., heart stimulation or vagal nerve stimulation, among others. In an example, the validation circuit 145 can interrogate ports 135 to determine the configuration of the leads 330.

Figure 4:
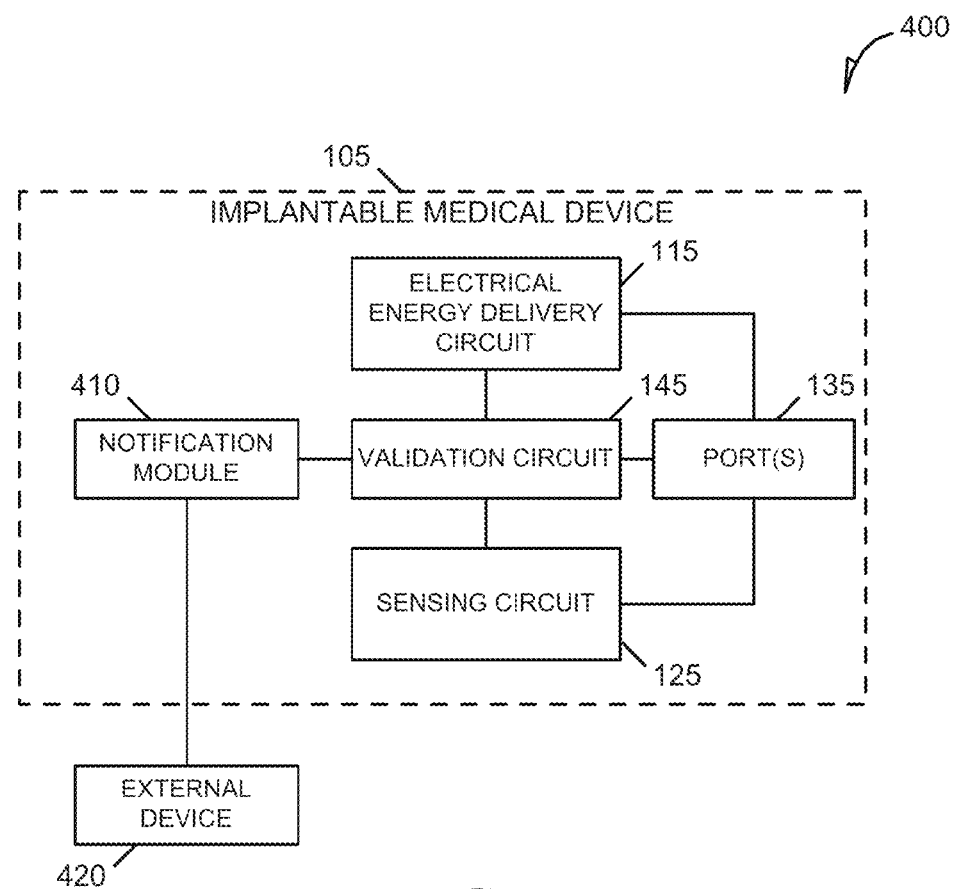
FIG. 4 illustrates generally an example of a system including an implantable device and an external device for configuring the implantable device based on port usage.

FIG. 4 illustrates generally an example of a system 400 including an implantable medical device 105 and an external device 420, where the external device 420 can be used for configuring the implantable medical device 105 based on port usage. In an example, the implantable medical device 105 includes the electrical energy delivery circuit 115, a sensing circuit 125, one or more ports 135, and a notification module 410. In this example, the notification module 410 can communicate the port configuration of the implantable medical device 105 to the external device 420. In an example, the notification module 410 can communicate the available programmable parameters of the implantable medical device 105 to the external device 420. In these examples, the implantable medical device 105 can use the validation circuit 145 to determine the configuration of leads connected to the ports 135. The implantable medical device 105 can then use the determined port configuration to enable or disable certain programmable parameters. The enabled or disabled programmable parameters can then be sent to the external device 420 via the notification module 410.

Figure 5:
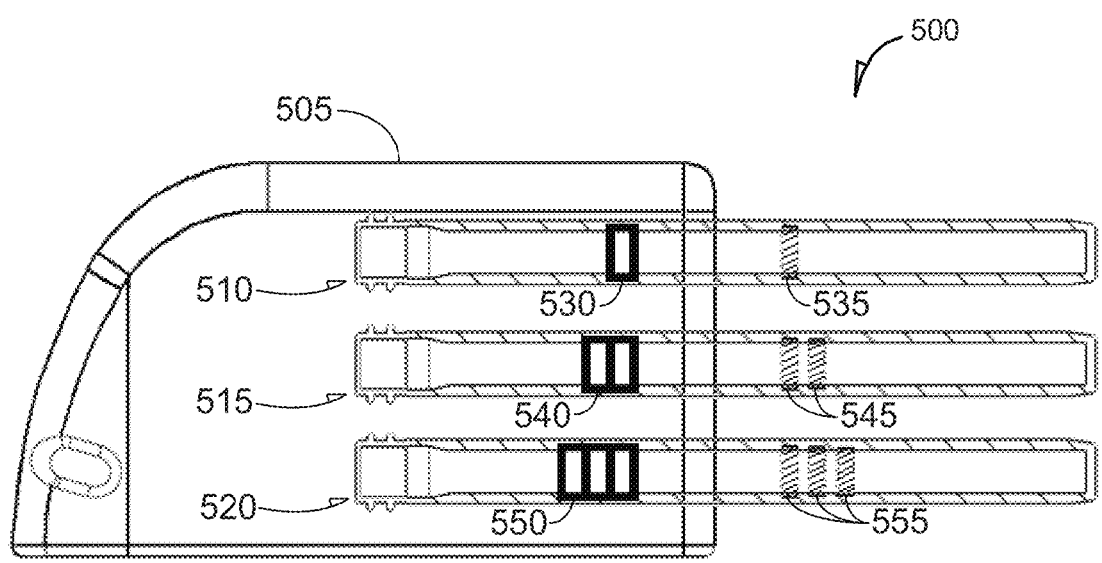
FIG. 5 illustrates generally an example of a system including an implantable device header with ports for connecting leadwires, catheters, or sensors.

FIG. 5 illustrates generally an example of a system 500 including an implantable device header 505 with ports 510, 515, 520 for connecting leadwires, catheters, or sensors. The system 500 illustrates a mechanical or electrical lead connection mechanism, which can be used by implantable medical device 105 to determine lead configuration. In an example, ports 510, 515, 520 can include mechanical interlocks 530, 540, 550 that mate with corresponding mechanical features 535, 545, 555, on the leads. In another example, the ports 510, 515, 520 can include electrical sensing mechanisms 530, 540, 550, which can sense the presence of unique features on the leads, such as those shown at 535, 545, 555. In an example, lead identification can be accomplished with unique electrical or mechanical connections not specifically shown in FIG. 5. Unused ports can also be identified through the use of mechanical or electrical connections. For example, a port plug can be used to short circuit electrical contacts within the port (which are normally used to electrically connect leads). In an example, the port plug creates a short circuit that can be sensed by the validation circuit 145 to determine that the port is unused. In another example, a port plug can be configured to have known impedance (when measured across certain port connections). In yet other examples, a port plug can cause an open circuit across certain port connections and thus provide an indication of an unused port.

In an example using an eight (8) electrode Precision™-type header port (from Boston Scientific Corporation, Natick, Mass.), the header port can have contacts (terminals) 1 and 2 dedicted to delivering AMT bipolar through lead cuff electrodes, contacts 3 and 4 can be dedicated to neural sensing, contact 5 dedicated to sensing a wide-vector ECG (electrocardiogram) between the lead electrode and the hosting of the implantable medical device, and contacts 6, 7, and 8 used in a binary code to indicate what lead(s) has been implanted. For example, a "0" represents an open circuit between contacts and a "1" represents a short circuit between contacts (e.g., the short circuit can be designed into the lead either by having the contact in the lead spread over two contacts in the header or by wiring a short-circuit into the lead). This configuration results in 5 unique binary combinations instead of the 8 normally available with three bits because short circuits involve two contacts. Thus, in an example, the five possible configurations for each port can include, '000' no lead in port, '001' AMT-only with 60 mm AMT electrodes, '010' AMT-only with 80 mm AMT electrodes, '100' AMT with wide-vector ECG and 60 mm AMT electrodes, '111' AMT with wide-vector ECG and 80 mm AMT electrodes.

In another example using a four (4) electrode header port (referred to as and IS-4 standard (ISO 5841-3:2000)), the header port can have contacts 1 and 2 dedicted to delivering therapy and contacts 3 and 4 used to determine lead type. For example, contacts 3 and 4 measuring an open circuit can indicate a cardiac lead is connected. Alternatively, if contacts 3 and 4 measure a short-circuit it can indicate that an AMT lead is connected.

The examples above can also include a lead design with a defined impedance between contacts within a port. Using a defined impedance approach can result in much greater number of possible combination (at least greater than the 5 or 2 lead design possibilities described above). Additionally, within an example, fluid ingress is a possibility that can be accounted for, such as where technically "open" contacts register some level of impedance due to the fluid induced conduction path between the contacts.

Figure 6:
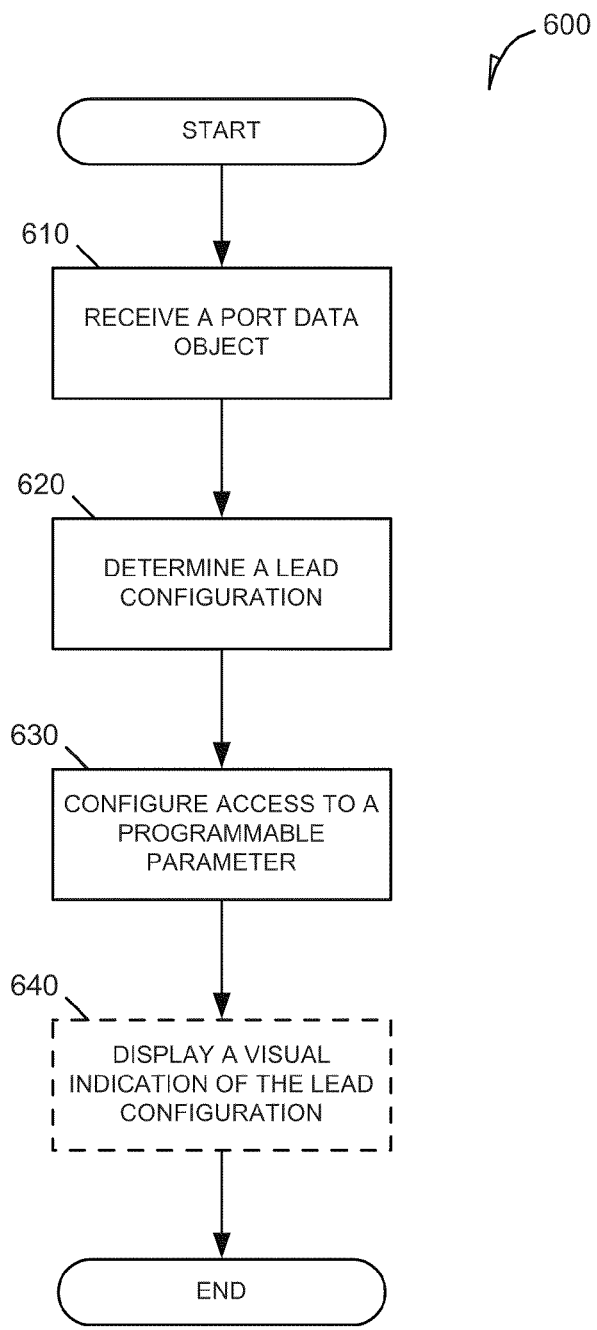
FIGS. 6-9 illustrate examples of automatically configuring programmable parameters of an implantable medical device according to port usage.

FIG. 6 is a flowchart illustrating a method 600 of configuring an implantable medical device 105 based on port usage, according to an example embodiment. In an example, the method 600 includes operations for receiving a port data object at 610, determining a lead configuration at 620, configuring access to a programmable parameter at 630, and optionally displaying a visual indication of the lead configuration at 640. In an example, the method 600 can begin at operation 610 with the external device 350 receiving a port data object from the implantable medical device 105. The port data object can include information regarding port configuration of the implantable medical device 105. At 620, the method 600 continues with the external device 350 determining a lead configuration for the implantable medical device 105 from the port data object. At 630, the method 600 continues with the external device 350 configuring access to programmable parameters of the implantable medical device 105 based on the determined lead configuration. In an example, configuring access to programmable parameters can include enabling or disabling certain user interface screens, the user-interface screens can include programmable elements displayed to a user of the external device 350. For example, a physician can use the external device 350 to program the implantable medical device 105. In this example, the external device 350 can restrict access to programmable features of the implantable medical device 105 that are not supported by the current lead configuration. At 640, the method 600 can conclude with the external device 350 displaying a visual indication of the lead configuration determined for the implantable medical device 105. In certain examples, the visual indication can be a graphical representation of the implantable medical device header, such as header 505. In an example, the visual indication can include descriptive textual information with or without a graphical display.

Figure 7:
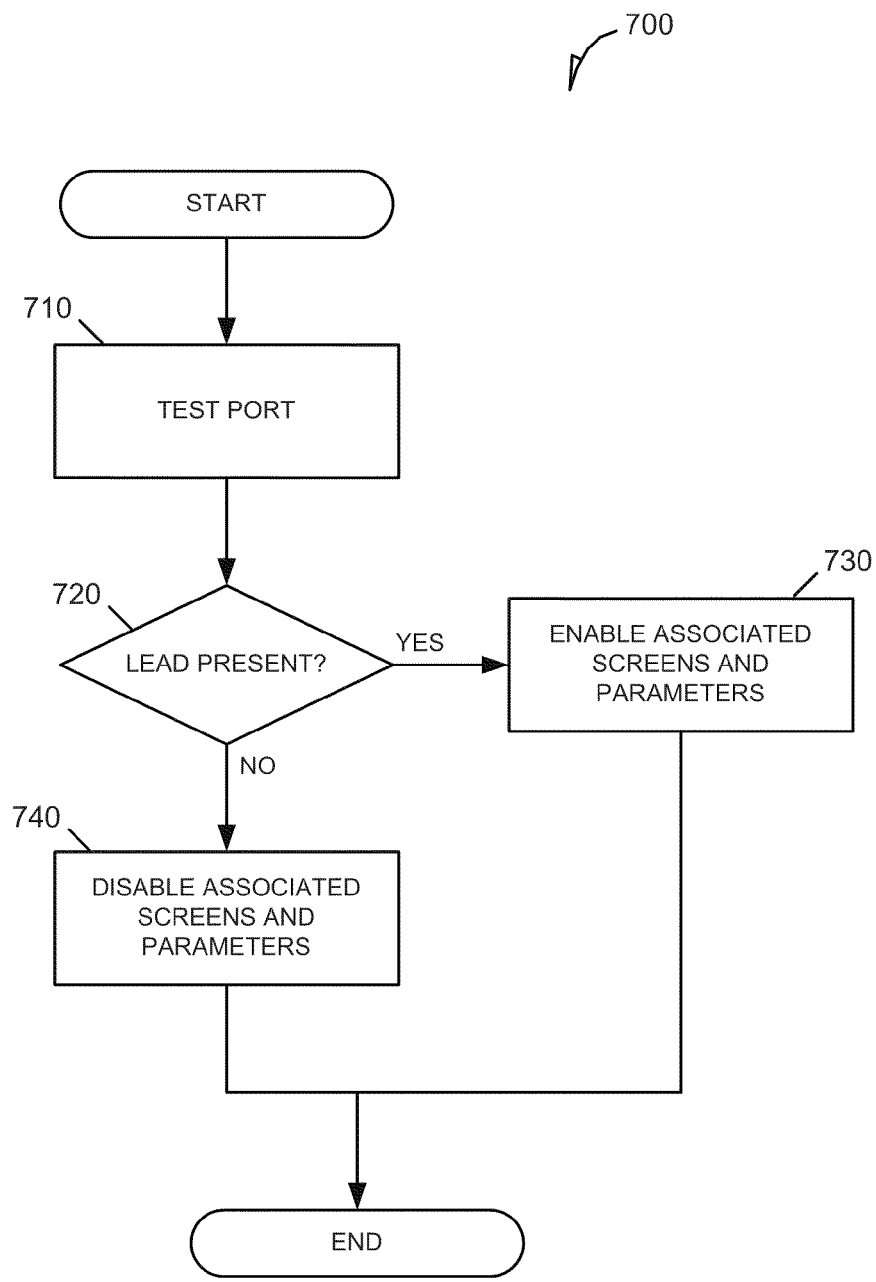

FIG. 7 is a flow chart illustrating an example method 700 for testing one or more ports 135 used to connect one or more leads to an implantable medical device 105 and configuring the implantable medical device 105 based on the type of leads connected to the ports 135. In an example, the method 700 includes operations for testing the port at 710, determining whether a lead is present at 720, enabling associated screens and/or parameters at 730, and disabling associated screens and/or parameters at 740.

In an example, the method 700 can begin at 710 with the implantable medical device 105 testing each of one or more ports 135. Testing can include obtaining an impedance measurement across electrical contacts within each port. In an example, testing can also include checking manual override switches associated with each of the one or more ports 135. In an example, testing each port can involve checking for mechanical features associated with each lead. In an example, testing can include making other electrical or mechanical measurements of a lead connected to one of the ports 135. In an example, the leads can contact mechanical interconnections within a port, e.g., spring contacts, which determine the lead type.

At 720, the method 700 continues with the implantable medical device 105 determining whether a lead is present in the port tested at 710. In an example, the implantable medical device 105 can also determine what type of lead is connected to one of the ports 135 by evaluating one of the measurements obtained at operation 710. For example, if an impedance measurement was taken at operation 710, the implantable medical device 105, e.g., the validation circuit 145 or the processor 310, can determine from the measurement what type of lead, if any, is present in the tested port, of the ports 135. If the implantable medical device 105 determines at operation 720 that no lead is present the method 700 continues at operation 740.

At 740, the method 700 continues with the implantable medical device 105 disabling user interface screens or programmable parameters associated with the unused port. In an example, the implantable medical device 105 can disable user interface screens or programmable parameters if a certain type of lead is detected as being connected to the tested port at operation 720. For example, if the tested port is determined at operation 720 to have an impedance measurement of 60Ω then at operation 740 the implantable medical device 105 can limit the amount of stimulation energy the physician can configure the implantable medical device 105 to deliver.

If the method 700 determines at operation 720 that a lead is connected to the tested port the method 700 can continue at operation 730. At 730, the method 700 continues with the implantable medical device 105 enabling user interface screens or programmable parameters associated with the type of lead determined to be connected to the tested port. In an example, the lead determined to be connected to the tested port can be a physiological sensor or similar device used to detect some physiological characteristic associated with delivering one of the therapies implantable medical device 105 is capable of providing.

In an example, the method 700 can loop multiple times in order to test each of the one or more ports 135. In this example, the method 700 can conclude when all the ports 135 associated with the implantable medical device 105 have been tested. In the example depicted in FIG. 7, the method 700 concludes after testing a single port of the one or more ports 135.

Figure 8:
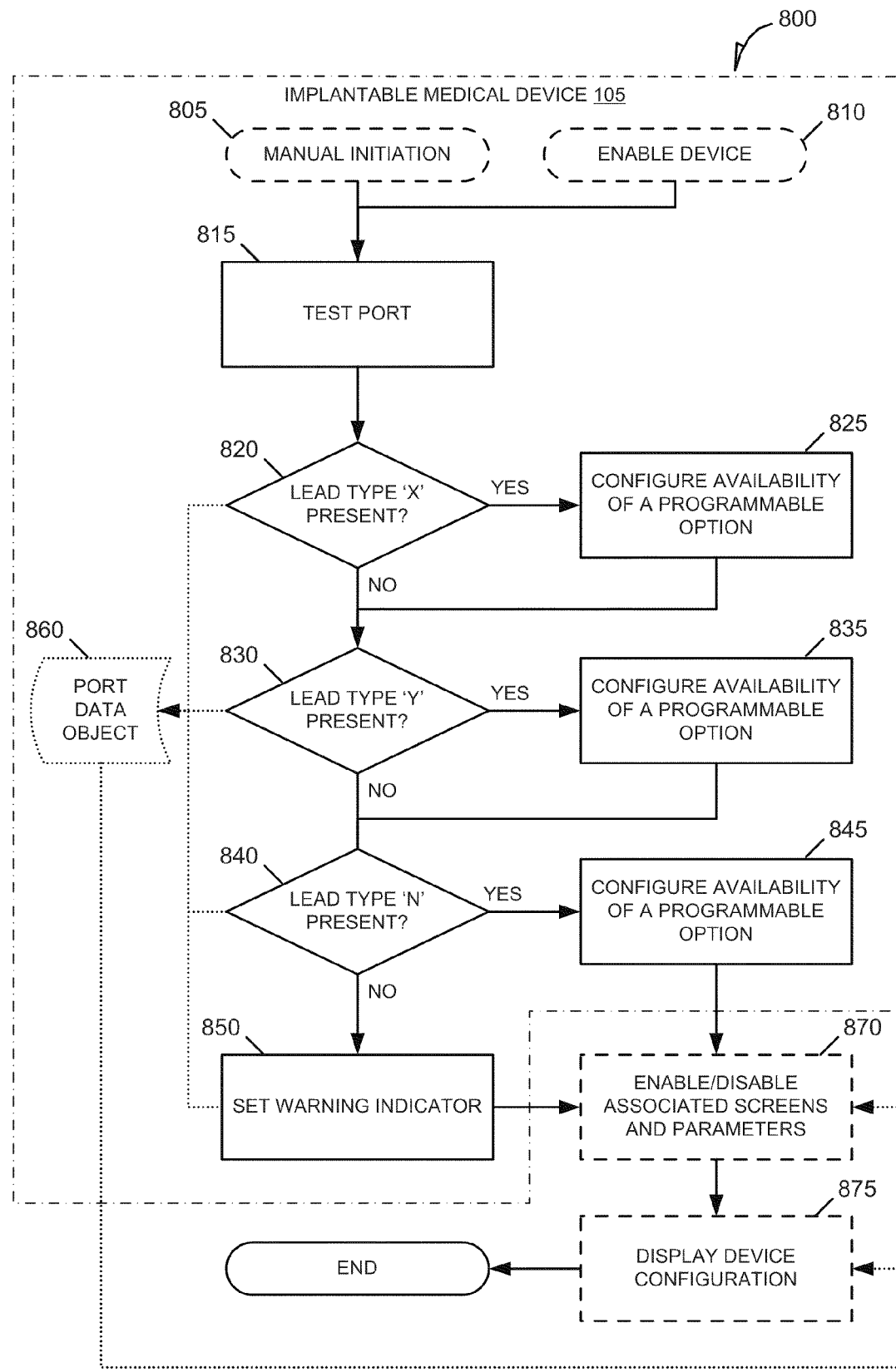

FIG. 8 illustrates generally a method 800 for configuring the availability of programmable features of an implantable medical device 105 according to the configuration of leads connected to the ports 135 of the implantable medical device 105. In this example the method 800 includes operations for testing a port at 815, determining whether a certain type of lead is present at 820, 830, and 840, configuring the availability of programmable options associated with the lead type at 825, 835, and 845, and setting a warning indicator if the lead type cannot be determined at 850. The method 800 also optionally includes operations for enabling or disabling user-interface screens or programming parameters associated with the detected lead configuration at 870 and displaying the detected device and/or lead configuration at 875. Additionally, the method 800 can be started automatically (not shown), by manual initiation at 805, or when the implantable medical device 105 is enabled at 810.

In an example, the method 800 begins at 815 with the validation circuit 145 within the implantable medical device 105 testing one or more of the ports 135. At 820, the method 800 continues with the processor 310 receiving the results of the port test from the validation circuit 145 and determining whether a lead of a particular type is connected to the tested port. For example, the processor 310 can receive an impedance measurement from the validation circuit 145 and from the impedance measurement determine that an AMT multiple contact lead is connected to the tested port. As depicted by operations 830 and 840 many different lead types can be detected with method 800. Once the type of lead is detected, for example through operations 820, 830, or 840, the processor 310 can optionally store the port (or lead) configuration information within a port data object 860.

In an example, at 825, the method 800 can continue with the implantable medical device 105 configuring the availability of programmable options associated with the detected lead type, e.g., lead type 'X' is this example. As depicted by FIG. 8, method 800 can continue at operations 835 or 845 if the detected lead type is 'Y' or 'N' respectively. For each different lead type detected as being connected to a tested port the appropriate associated programmable options can be made available by the implantable medical device 105. In an example, the lead type and associate therapy type are determined at operations 820, 830, and 840.

At 850, the method 800 continues with the processor 310 setting a warning indicator if the configuration of the tested port cannot be determined automatically. In an example, the warning indicator can signal a treating physician of a device malfunction or simply indicate that the physician must manually determine the implantable device configuration.

Optionally, the method 800 continues at 870 with an external programming device, such as external device 350, receiving the port usage information, e.g., the port data object 860. At 870, the external device 350 can use the port data object 860 to enable or disable associated user-interface screens and/or programmable parameters based on port usage information determined by the implantable medical device 105. At 875, the method 800 optionally continues with the external device 350 displaying the configuration of the implantable device (see FIGS. 10A-10C for example graphical displays).

In an example, the port configuration information determined by the validation circuit 145 and/or the processor 310 can be stored within a port data object 860. The port data object 860 can be sent to an external device, such as external device 350, where the availability of programmable options can be configured accordingly. For example, the validation circuit 145 can measure the impedance across particular electrical contacts within the tested port and the processor 310 can store the measurement in the port data object 860. The port data object 860 can be sent to the external device 350, where the external device 350 can extract the impedance measurement and determine that a lead of type 'Y' is connected to the port.

Figure 9:
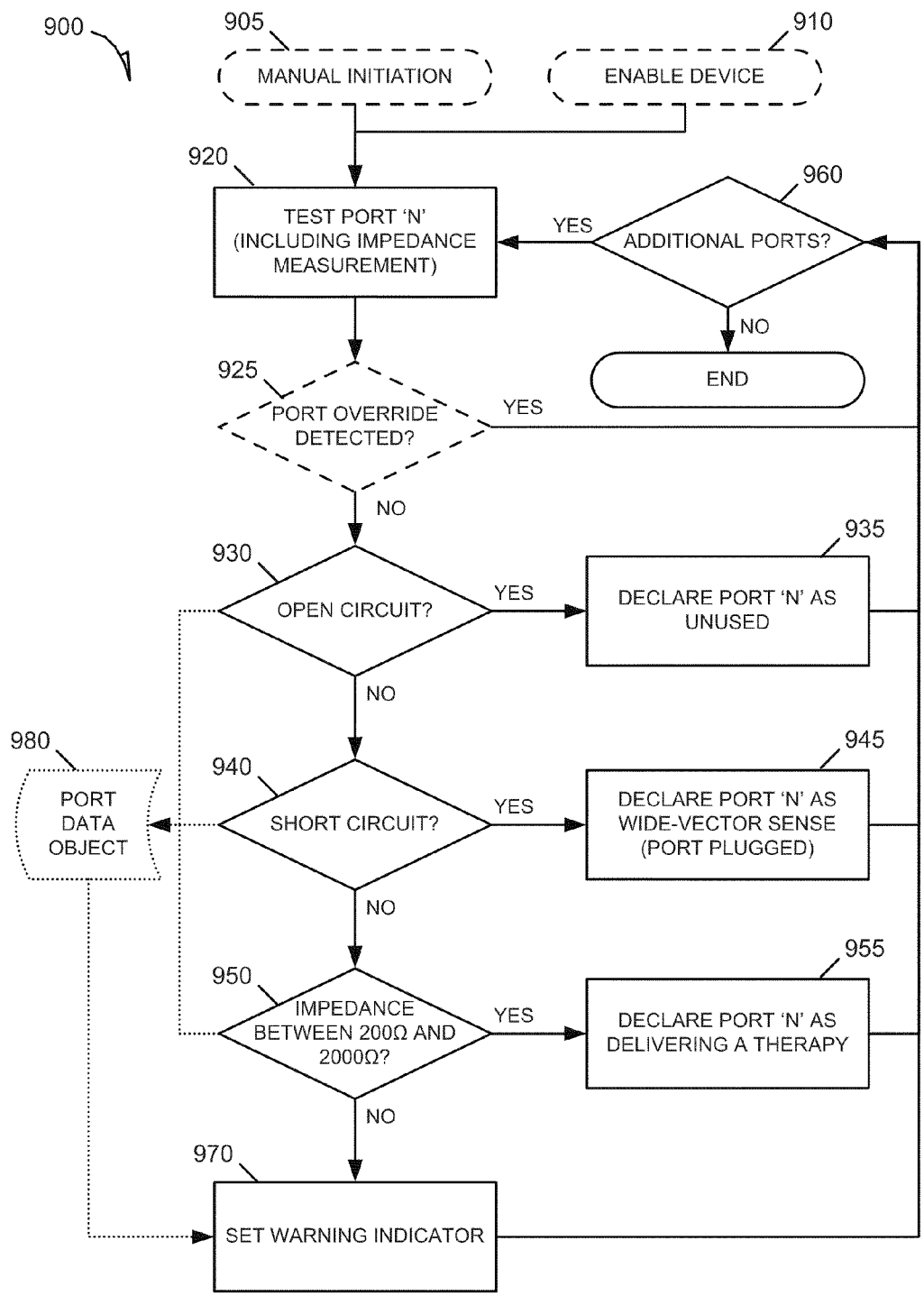

FIG. 9 illustrates generally a method 900 for configuring the availability of programmable features of an implantable medical device 105 according to the configuration of leads connected to the ports 135 of the implantable medical device 105. In an example, the method 900 includes operations for testing a port at 920, determining if the port test indicates an open circuit at 930, declaring the tested port as unused at 935, determining if the port test indicates a short circuit at 940, declaring the tested port as providing a wide-vector sense at 945, determining if the port test returns an impedance within a certain range at 950, declaring the tested port as delivering a certain therapy at 955, determining if additional ports need to be tested at 960, and setting a warning indicator at 970.

In an example, the method 900 can be started by manual initiation at 905 or automatically when the implantable medical device 105 is enabled at 910. At 920, the method 900 continues with the validation circuit 145 testing the first of 'N' ports for connecting leads to the implantable medical device 105. As noted above, the implantable medical device 105 can include one or more ports. Combined therapy devices often include between two and five ports for connecting leads and/or sensors. However, the current subject matter can function over an unlimited number of ports. Each port within an implantable medical device can include between 2 and 8 contacts or terminals for making electrical connections with the leads. For examples, IS-1 (ISO 5841-3:2000) and DF-1 (ISO 11318:2002) ports include 2 contacts, while IS-4 ports include 4 contact. The Precision™ ports, discussed above, include 8 contacts.

At 925, the method 900 can optionally include detection of port override mechanisms. A port override mechanism can include a mechanical or electrical switch used by an implanting physician to limit the functionality of a lead or sensor connected to affected port. For example, a port configured to deliver a stimulation therapy can include an override mechanism that limits the amount of stimulation energy that can be delivered through the port by the electrical energy delivery circuit 115. In an example, a port can be configured to deliver both stimulation therapy, e.g., cardiac pacing stimulation, and sense intrinsic electrical signals, but an implanting physician can set an override switch to prevent the port from delivering stimulation therapies. For example, a physician can implant a lead capable of both cardiac sensing and pacing in a location other than within cardiac tissue. The lead can be used to sense ECG-like signals, but sending pacing energy out on the electrode can result in operational challenges for the device. In another example, a port can include an override mechanism that indicates that the port is unused.

At 930, the method 900 continues with the validation circuit 145 testing the port for an open circuit. If an open circuit is detected at 930, the method 900 continues at 935 by declaring the port as unused. If the validation circuit 145 does not determine that an open circuit exists at 930 the method 900 continues at 940. The method 900 continues at 940 with the validation circuit 145 testing the port for a short circuit across a set of electrical contacts in the port. If a short circuit is detected at 940, method 900 continues at 945 with the validation circuit 145 or the processor 310 declaring the port as configured for a wide-vector sense. Alternatively, at 945 the validation circuit 145 or the processor 310 can declare port as is being plugged, e.g., with a port plug. If the validation circuit 145 does not detect a short circuit at 940, the method 900 continues at 950 with the validation circuit 145 taking an impedance measurement across electrical contacts within the tested port. If at 950 validation circuit 145 detects impedance within a specified range the method 900 continues at 955 with the validation circuit 145 or the processor 310 declaring the port as being configured to deliver a certain therapy. For example, if the validation circuit 145 determines the impedance to measure between 200Ω and 2000Ω than the processor 310 can declare the port as being configured with a cardiac stimulation (pacing) lead. In another example, if the validation circuit 145 determines the impedance to measure between 20Ω and 120Ω the processor 310 can declare the port as being configured with a cardiac shocking electrode.

At 970, the method 900 continues with the processor 310 setting a warning indicator if the port being tested is not found to conform to any of the tests performed by the validation circuit 145 at operations 925, 930, 940 or 950. At 960, the method 900 continues with the processor 310 determining whether any additional ports need to be tested. As depicted in FIG. 9, the method 900 loops back to operation 960 after the configuration of each port is determined. In an example, the implantable medical device 105 can include switches associated with each port that are set by the implanting physician and control whether the port will be tested to determine the configuration of the port, e.g., the type of lead connected to the port.

In this example, the method 900 can include the validation circuit 145 or the processor 310 collecting port configuration data and storing it within a port data object 980. In an example, the port data object 980 can be used by the implantable medical device 105 or the external device 350 to configure access to certain programmable parameters associated with the implantable medical device 105.

Figure 10A:
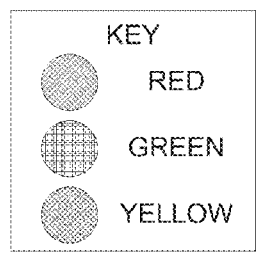
FIGS. 10A-10C illustrate generally examples of graphical indicators of port usage for an implantable medical device.
Figure 10A:
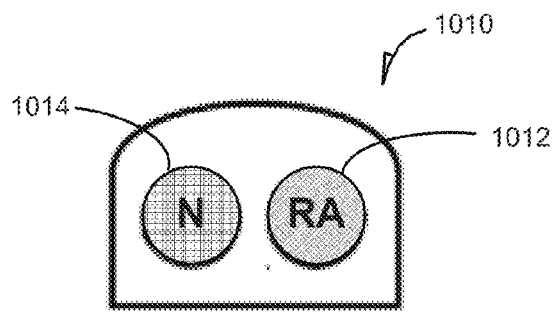

FIG. 10A illustrates generally an example of a graphical indicator of port usage for an implantable medical device 105. In an example, the external device 350 can include user-interface screens that allow a treating physician to program the implantable medical device 105. The user-interface screens can include a graphical display of the implantable device configuration based on port usage, such as that shown by an implantable medical device header graphic 1010. The implantable medical device header graphic 1010 includes port indicators 1012 and 1014. In this example, port indicator 1012 is displaying "RA" and can be color coded, such as colored red. In an example, RA stands for Right Atrium, indicating that the lead connected to this port is configured to provide stimulation to the right atrium of the patient's heart. In this example, port indicator 1014 is displaying "N" and can be color coded, such as colored green. In an example, N can be interpreted as Neural, indicating that the lead connected to this port is configured to provide neural stimulation, such as to the vagal nerve. Alternatively, the N in combination with the green color coding can indicate that the connected lead is configured to sense electrical activity at a neural tissue site. The implantable medical device header graphic 1010 can also include descriptive icons and additional text to visually provide additional configuration information. For the purposes of this application, a graphical display contains some form of visual information beyond simple text, e.g., a picture, an icon, a drawing, or color coding, among others.

Figure 10B:
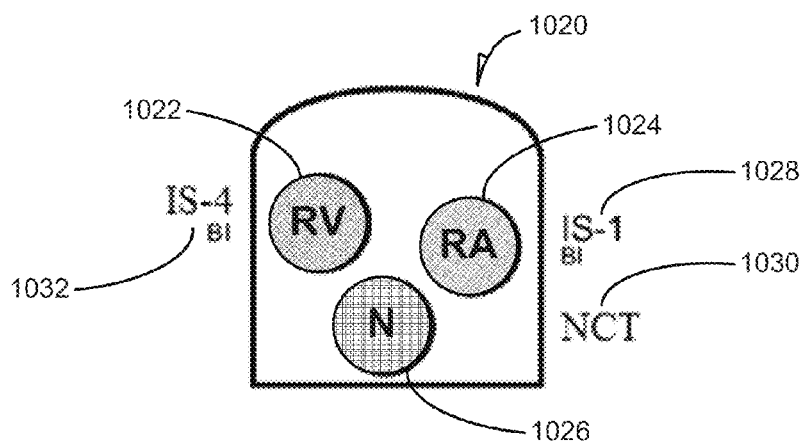

FIG. 10B illustrates generally an example of a graphical indicator of port usage for an implantable medical device 105. In this example, an implantable medical device header graphic 1020 includes three port indicators 1022, 1024, and 1026. Port indicators 1024 and 1026 illustrate similar graphical displays as discussed above in reference to port indicators 1012 and 1014 respectively. However, port indicators 1024 and 1026 include some additional descriptive text. For example, port indicator 1024 includes descriptive text 1028, which includes "IS-1" and "BI." In an example, "IS-1" can represent that the port conforms with connector standard ISO 5841-3:2000. In an example, "BI" can represent a bipolar configuration. Port indicator 1026 includes descriptive text 1030, which includes "NCT." In an example, "NCT" can represent NeuroCardiac Therapy (also known as Autonomic Modulation Therapy), further defining what type of lead is connected to the port represented by port indicator 1026.

In this example, port indicator 1022 is displaying "RV" and can be color coded, such as colored yellow. Port indicator 1022 can also include additional descriptive text, such as descriptive text 1032. In this example, descriptive text 1032 includes "IS-4" and "BI" (IS-4 indicates conformance with a pending connector standard ISO 27186). In an example, descriptive text 1028, 1030, and 1032 can be replaced by descriptive icons or additional descriptive pictures.

Figure 10C:
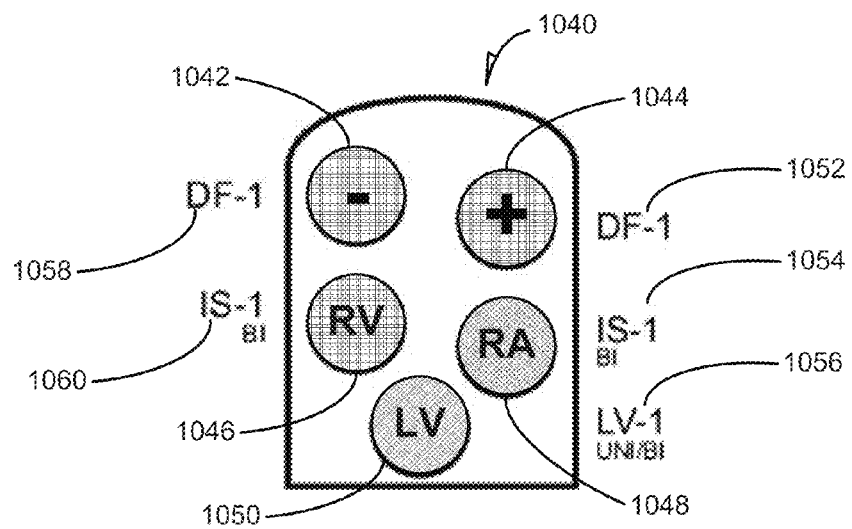

FIG. 10C illustrates generally an example of a graphical indicator of port usage for an implantable medical device 105. In this example, an implantable medical device header graphic 1040 includes five port indicators 1042, 1044, 1046, 1048, and 1050. In this example, the port indicator 1042 includes a "−" (minus) sign and can be color coded, such as colored green. Port indicator 1042 also includes descriptive text 1058, which reads "DF-1." The port indicator 1042 (minus sign) and the descriptive text 1058 combination can be interpreted to indicate that the lead connected to this port is the negative electrical connection for a defibrillation lead. In this example, the port indicator 1044 includes a "+" (plus sign) and can be color coded, such as colored green. The port indicator 1044 (plus sign) also includes descriptive text 1052, which reads "DF-1." The port indicator 1044 (plus sign) and the descriptive text 1052 in combination can be interpreted to indicate that the lead connected to this port is the positive electrical connection for a defibrillation lead.

In this example, the port indicator 1048 includes an "RA" indicating that the lead connected to this port is in the right aorta of the patient's heart. The port indicator 1048 also includes descriptive text 1054, which provides additional characterization of the lead type connected to this port. This example also includes port indicator 1046, which includes an "RV" indicating that the lead connected to this port is in the right ventricle of the patient's heart. Port indicator 1046 also includes descriptive text 1060.

In this example, the port indicator 1050 includes an "LV" indicating that the lead connected to this port is in the left ventricle of the patient's heart. The port indicator 1050 also includes descriptive text 1056, which reads "LV-1" and "UNI/BI" (UNI indicates a unipolar configuration).

Example External Device and Machine-Readable Medium

Figure 11:
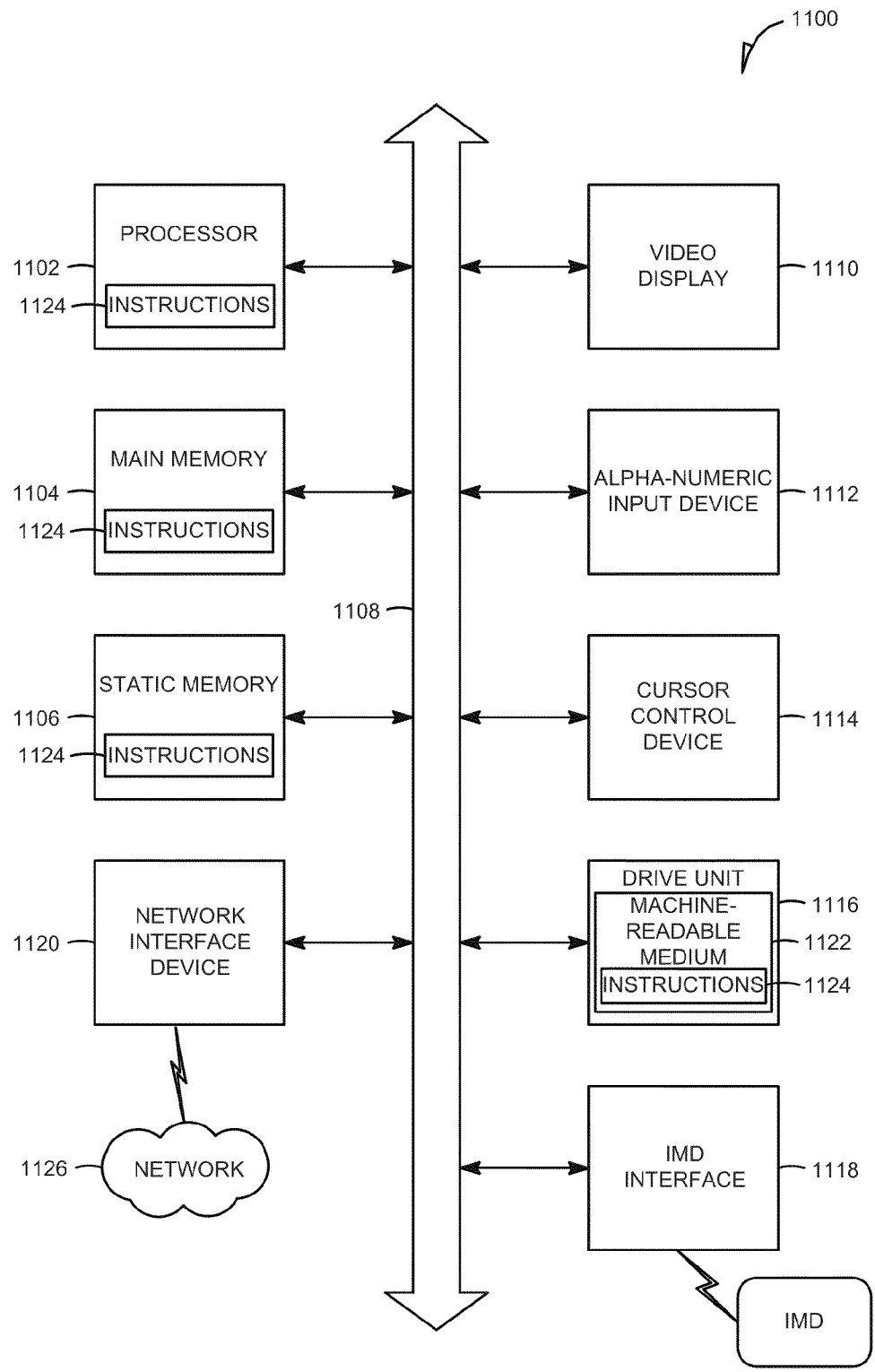
FIG. 11 is a block diagram illustrating an example external computing device for communicating with an implantable medical device.

FIG. 11 is a block diagram illustrating an example of an external communication and storage device. The system 1100 is a machine in the example form of a computer system 1100 within which instructions, for causing the machine to assist in the performance of any one or more of the methodologies discussed herein, may be executed. In an example, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the machine can include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 can further include a video display unit 1110 (e.g., a liquid crystal display (LCD) or a cathode ray tube (CRT)). The computer system 1100 also includes an alphanumeric input device 1112 (e.g., a keyboard), a user interface (UI) navigation device 1114 (e.g., a mouse), a disk drive unit 1116, an implantable medical device interface 1118, and a network interface device 1120. The implantable medical device interface can include a wired or wireless data connection with an implantable medical device. In an example, the system 1100 includes both a wired and a wireless data connection with an implantable medical device. In an example, the implantable medical device (IMD) interface allows information stored in the IMD to be downloaded to the computer system 1100 for storage and/or re-transmission to a treating physician or patient management system. In an example, the information downloaded from the IMD can be displayed on the video display unit 1110. In another example, the information downloaded can be processed by the processor 1102 prior to display on the video display unit 1110. In an example, the IMD interface can also upload information, including programming parameters for an implantable CRM device, back into the IMD.

Machine-Readable Medium

The disk drive unit 1116 includes a machine-readable medium 1122 on which can be stored one or more sets of instructions and data structures (e.g., software) 1124 embodying or utilized by any one or more of the methodologies or functions described herein. The instructions 1124 can also reside, completely or at least partially, within the main memory 1104 or within the processor 1102 during execution thereof by the computer system 1100, the main memory 1104 and the processor 1102 also constituting machine-readable media.

While the machine-readable medium 1122 can be shown in an example embodiment to be a single medium, the term "machine-readable medium" can include a single medium or multiple media (e.g., a centralized or distributed database, or associated caches and servers) that store the one or more instructions or data structures. The term "machine-readable medium" can include any tangible medium that is capable of storing, encoding or carrying instructions for execution by the machine and that cause the machine to perform any one or more of the methodologies of the present application, or that is capable of storing, encoding or carrying data structures utilized by or associated with such instructions. The term "machine-readable medium" can include, but need not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks including internal hard disks and removable disks; magneto-optical disks; and CD-ROM and DVD-ROM disks.

Transmission Medium

The instructions 1124 can further be transmitted or received over a communications network 1126 using a transmission medium. The instructions 1124 can be transmitted using the network interface device 1120 and any one of a number of transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., Wi-Fi and WiMax networks).

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. An example can include a computer-readable medium, a processor-readable medium, or a machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like. In an example, the methods can be performed on an implanted or embedded device. In these examples, the code can be stored on a processor-readable medium for execution by the implanted or embedded device.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Device Oriented Examples:

Example A. A medical device comprising:
  a validation circuit configured to test a port to obtain a port parameter, the port capable of connecting a lead to the medical device;
  a processor configured to:
  receive the port parameter obtained by the validation circuit;
  automatically determine, based on the port parameter, a device lead configuration; and
  configure, based on the device lead configuration, availability of a programmable parameter.

Example B. The medical device of Example A, further including a notification module configured to generate a configuration notification, based the availability of the programmable parameter.

Example C. The medical device of Example C, wherein the notification module is configured to send the configuration notification to an external device.

Example D. The medical device of Example A, wherein the validation circuit tests the port to obtain an impedance measurement.

Example E. The medical device of Example D, wherein the processor automatically determines the device lead configuration based on determining whether the impedance measurement indicates one of the following conditions:
  an open circuit;
  a short circuit; or
  a pre-determined range of impedance values.

Example F. The medical device of Example A, wherein the validation circuit is configured to test for the presence of a port plug, wherein the port plug has a pre-defined attribute measurable by the validation circuit.

The claimed invention is:

1. A system comprising:
an external device configured to communicate with an implantable medical device, the external device including:
  a processor; and
  a memory, coupled to the processor, comprising instructions, which when executed by the processor cause the processor to:
  receive from the implantable medical device a port data object, the port data object including information about whether a port of the implantable medical device is electrically coupled to a lead;
  determine, based on the port data object, a lead configuration associated with the implantable medical device; and based on the determined lead configuration, enable or inhibit access to a programmable parameter of the implantable medical device.

2. The system of claim 1, wherein the external device receives the port data object including a measurable attribute associated with individual ones of the plurality of ports represented within the port data object.

3. The system of claim 2, wherein the measurable attribute associated with individual ones of the plurality of ports is impedance.

4. The system of claim 3, wherein the external device determines the lead configuration based on determining whether the impedance measurement associated with individual ones of the plurality of ports indicates one of the following conditions:
an open circuit;
a short circuit; or
a pre-determined range of impedance.

5. The system of claim 1, wherein the external device determines the lead configuration based on detecting whether the port data object includes a manual override indicator for any of the plurality of ports, wherein the manual override indicator indicates that the port is unused.

6. The system of claim 1, wherein the external device determines the lead configuration based on determining a therapy type; and
wherein the external device enables or inhibits access to a plurality of programmable parameters based on the determined therapy type.

7. The system of claim 1, further comprising a display device, communicatively coupled to the external device, the display device configured to display a visual indication of the lead configuration of the implantable medical device.

8. The system of claim 7, wherein the display device displays a graphical display representing the lead configuration of the implantable medical device.

9. The system of claim 1, wherein the external device determines a lead configuration based on determining, from the port data object, whether a port is configured for a type of use selected from a group of potential uses including:
unused;
sense-only;
therapy only; and
therapy with sensing.

10. The system of claim 1, wherein the external device determines a lead configuration based on determining, from the port data object, whether a lead connected to a port includes a therapy output restriction.

11. A non-transitory processor-readable storage medium comprising instructions, which when implemented by one or more processors perform the following operations:
receive from an implantable medical device a port data object, the port data object containing information about whether a port of the implantable medical device is coupled to a lead;
determine, based on the port data object, a lead configuration associated with implantable medical device;
based on the determined lead configuration associated with the implantable medical device, enable or inhibit access to a programmable parameter of the implantable medical device; and
display, using an external device configured to communicate with the implantable medical device, a visual indication of the lead configuration of the implantable medical device.

12. The processor-readable storage medium of claim 11, wherein the port data object includes a measurable attribute for the port.

13. The processor-readable storage medium of claim 12, wherein the measurable attribute for the port is impedance.

14. The processor-readable storage medium of claim 13, wherein the operation to enable or inhibit access to the programmable parameter includes determining whether the impedance measurement indicates one of the following conditions:
an open circuit;
a short circuit; or
an impedance being within a specified range of impedance.

15. The processor-readable storage medium of claim 11, wherein the port data object includes a manual override indicator, the manual override indicator indicates a lead configuration for a port of the implantable medical device.

16. The processor-readable storage medium of claim 11, wherein the operation to determine the lead configuration includes determining a therapy type; and
wherein the operation to enable or inhibit access to the programmable parameter includes enabling programmable parameters based on the therapy type.

17. The processor-readable storage medium of claim 11, wherein the visual indication of the lead configuration includes a graphical display representing the implantable medical device.

18. The processor-readable storage medium of claim 11, wherein the operation to determine the lead configuration includes determining whether a port is configured for one type of use from a group of potential uses including:
unused;
sense-only;
therapy only; and
therapy with sensing.

19. The processor-readable storage medium of claim 11, wherein the operation to determine the lead configuration includes determining a therapy output restriction associated with a port.

20. A method comprising:
receiving from an implantable medical device a port data object, the port data object including information about whether a port of the implantable medical device is coupled to a lead;
determining, based on the port data object, a lead configuration associated with the implantable medical device;
based on the lead configuration associated with the implantable medical device, enabling or inhibiting access to a programmable parameter of the implantable medical device; and
displaying, using an external device configured to communicate with the implantable medical device, a visual indication of the lead configuration of the implantable medical device.

* * * * *